United States Patent [19]

Bieringer et al.

[11] 4,424,441
[45] Jan. 3, 1984

[54] METHOD AND APPARATUS FOR INSPECTING GLASS CONTAINERS

[75] Inventors: Robert J. Bieringer; Sam Lovalenti, both of Toledo, Ohio

[73] Assignee: Owens-Illinois, Inc., Toledo, Ohio

[21] Appl. No.: 273,164

[22] Filed: Jun. 12, 1981

[51] Int. Cl.³ .............................................. G01V 9/04
[52] U.S. Cl. ................................. 250/223 B; 356/240
[58] Field of Search .................... 250/216, 223 B; 356/240; 209/524

[56] References Cited

U.S. PATENT DOCUMENTS

| 4,026,414 | 5/1977 | Ellinger | 356/240 |
| 4,256,957 | 3/1981 | Ford et al. | 250/223 B |
| 4,284,353 | 8/1981 | Yoshida et al. | 209/524 |
| 4,367,405 | 1/1983 | Ford | 250/223 B |

*Primary Examiner*—David C. Nelms
*Attorney, Agent, or Firm*—Gerald T. Welch; Myron E. Click

[57] ABSTRACT

This invention relates to method and apparatus for inspecting glass containers and other types of containers having transparent or translucent sidewalls for defects, and especially to inspecting the finish portion of glass containers for defects such as horizontal checks. The entire finish portion is illuminated by diffused light and the check-type defects reflect light upwardly into an Erfle eyepiece which is then imaged onto a matrix-type light sensor.

7 Claims, 3 Drawing Figures

METHOD AND APPARATUS FOR INSPECTING GLASS CONTAINERS

This invention relates to inspecting glass containers and other types of containers having transparent or translucent sidewalls for defects, and especially to inspecting glass containers for defects such as horizontal checks in the finish portion thereof.

BACKGROUND OF THE INVENTION

In the manufacture of glass containers, a defect that is sometimes found which is difficult to detect comprises a generally horizontal check or mirror-like flaw in the neck or finish portion of the container. It is essential that such defects or flaws be detected even though they be few in number, with respect to the total number of containers being manufactured.

The prior art has employed various types of inspection devices primarily relying on illuminating the defect and then reading the presence of reflected light emitted by the defect. The following U.S. patents all relate to such devices which are satisfactory to a greater or lesser degree in detecting defects, primarily to directing and reading the scattered light by altogether different forms of apparatus. The patents are:

U.S. Pat. No. 3,349,906—Calhoun et al.
U.S. Pat. No. 3,834,429—Schulz
U.S. Pat. No. 4,140,901—Fischer et al.
U.S. Pat. No. 4,213,042—Beach et al.

All of the aforesaid patents involve methods and apparatus which are substantially different and less effective than the present invention.

SUMMARY OF THE INVENTION

It is an object of the present invention to provide method and apparatus for quickly inspecting the finish portion of a hollow, transparent container for horizontal checks on the surface or buried in the walls thereof and rejecting those containers having such defects or flaws.

It is a further object of the present invention to provide such method and apparatus wherein glass containers can be inspected without rotation immediately after forming and annealing while they are relatively cool or at ambient temperature, following such operations.

Another object of the invention is to provide such method and apparatus which is relatively simple and economical whereby the finish area of containers can be inspected without rotation in a very expedient manner.

Generally, the invention comprises moving the hollow containers successively through an inspection station, momentarily interrupting the lateral movement of each container and retaining same stationarily upright at the inspection station, directing a concentrated source of radiant energy to which the container is transparent downwardly through the complete region of the finish portion to thereby illuminate the sidewalls thereof, and causing a portion of the light to be redirected upwardly axially by any existent checks. The redirected light is imaged onto a light-sensitive detector, such as a video camera stationarily mounted axially facing downwardly and adjacent to the container upper lip area. The redirected sensed light is detected by the sensor during stationary, non-rotational retention of the container at the inspection station and the sensor produces a reject signal for subsequent rejection of the flawed container.

DESCRIPTION OF THE PREFERRED EMBODIMENT

Figure 1:
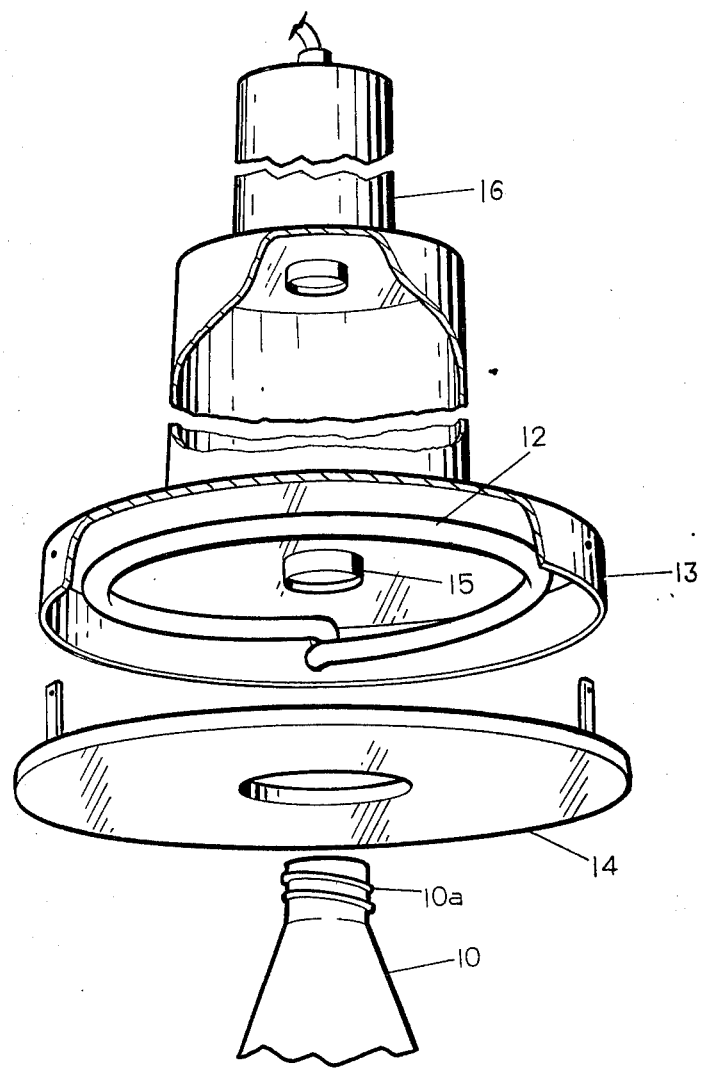
FIG. 1 is a diagrammatic perspective view of an apparatus embodying the present invention.
Figure 2:
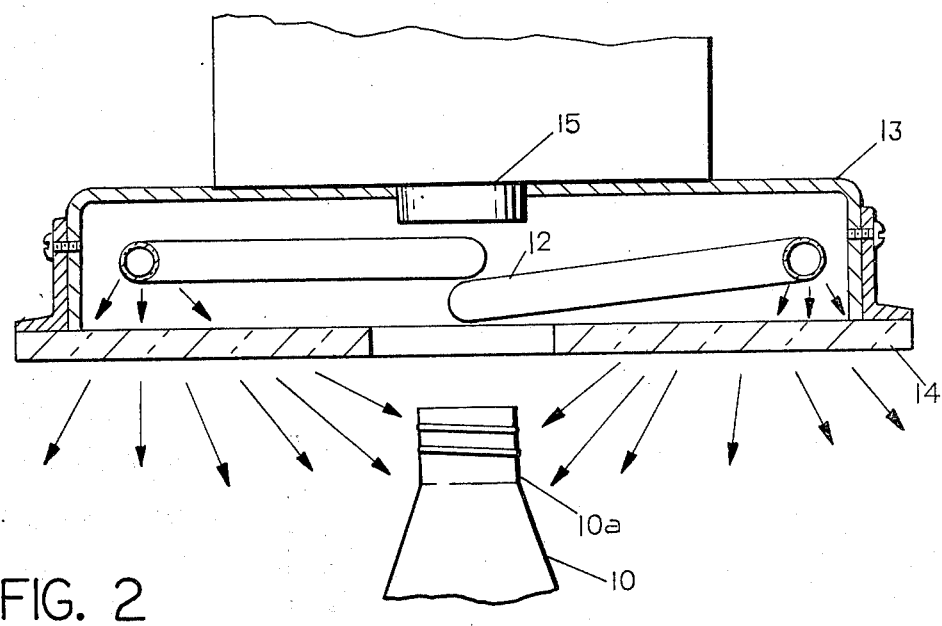
FIG. 2 is an enlarged vertical sectional view of the defect-bearing finish portion of the glass container being inspected, illustrating the manner in which the finish receives the diffused illuminating light.

Referring to the drawings, the containers 10 are adapted to be moved through an inspection station on a rotary inspection machine, such as by a starwheel mechanism, as is known in the art. The rotary inspection machine (not shown), and specifically its starwheel mechanism, moves each container 10 in upright position to the inspection station, as shown in FIG. 1. The container is preferably inspected while being moved laterally in-line without stoppage. However, its lateral movement may also be interrupted momentarily by stopping the starwheel for a required brief inspection interval. Normally, the containers are newly-formed but not sufficiently hot to require special handling techniques or non-checking materials to handle the same. The inspection is preferably conducted immediately following the annealing procedure to remove inherent stresses from the containers and while they are at ambient temperature.

When each container 10 is positioned at the inspection station, it is preferably resting upright on a non-rotatable disc or pad. With the container in proper position for inspection, a source of radiant energy such as provided by an incandescent source or flash lamp 12, in the form of an annular ring or circular tube, is mounted within a suitable hollow circular chamber 13. The lamp 12 is connected to a suitable power source such as a 110 V electrical line. A diffuser plate 14 in the form of a translucent circular disc is mounted beneath hollow chamber 13, with both the diffuser plate and the chamber having a central opening or aperture. The diffuser plate is mounted closely adjacent to and immediately over the finish portion 10a of the container in axial alignment therewith at the inspection station. The diffused light is transmitted into and through the finish portion 10a, the container being transparent to such transmitted light.

Figure 3:
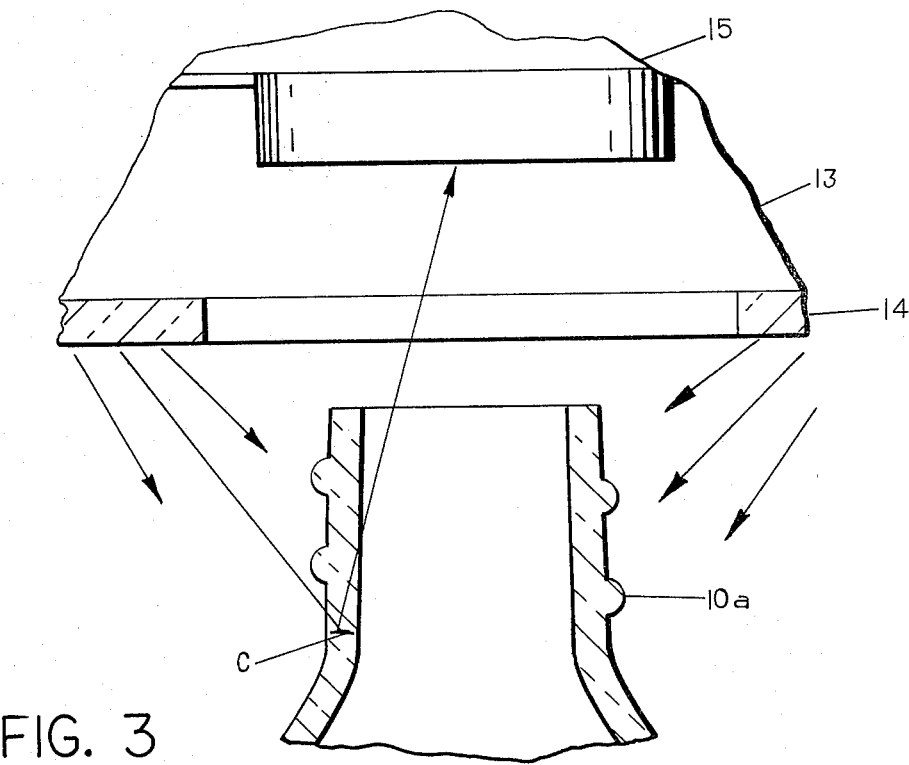
FIG. 3 is a further enlarged vertical sectional view of the defect-bearing finish portion, illustrating the manner in which the check-type defect reflects the diffused illuminating light.

The downwardly-directed diffused light passes into the interior portion of the container and brightly illuminates the same. If a defect or flaw, such as a horizontal check C is present in the finish of the container, a portion of the internally-transmitted light is redirected exteriorly upwardly through the central opening in diffuser plate 14 and chamber 13 into an Erfle lens 15. The lens is mounted within an upper region of chamber 13 to gather the upwardly redirected and reflected light from the check C as shown in FIG. 3. The light sensor 16 such as a video camera is sensitive to the radiant energy emitted by the light source and reflected by the defect C. The lens 15 serves to gather and concentrate the reflected light in the light sensor 16 to increase its sensitivity. If a defect such as a check C is present, the redirected portion of the light is caused to pass upwardly through the container surface exteriorly and vertically to be collected by the lens system and be detected by the sensor.

The sensor 16 comprising a video camera is preferably a video array camera. Such video camera is a matrix array of discrete light-sensitive diodes which view the container finish, such as a threaded bottle finish, in a horizontal direction. The diodes are sequentially electronically interrogated (scanned) to determine which diodes have seen an increase in light intensity which results in a greater output voltage from these diodes. One can then compare voltages from adjacent diodes or ratios of voltages to detect a bright signal and measure the intensity and location of the signal. The scan information is used to produce a reject signal. The reject signal serves to energize a reject mechanism mounted at a subsequent point along an off-loading conveyor which discharges the inspected containers.

The circular lamp element provides 360° illumination so that the container or bottle does not require rotation. The reflected light is gathered by an Erfle eyepiece (multi-element lens) which provides an extremely-wide field of view and excellent correction of all aberrations. The wide-angle field of view permits simultaneous imaging of the entire, nominally-cylindrical, wall of the finish portion of the container. Such system is known to provide excellent spherical and chromatic correction.

Thus, the present invention provides an improved method and apparatus for inspecting the finish area of hollow transparent containers for horizontal checks or interior flaws. Such defects can be efficiently and expediously determined in glass containers whether they be formed of clear fling glass or colored glass. Since the containers need not be rotated, the inspection can be achieved in a small fraction of a second for each container. In addition, the technique is applicable to non-round containers which are mechanically difficult to rotate. Defects, whether they be relatively small or large, so long as they exhibit an appreciable horizontal component, can be detected by the present invention. The circular lighting element and diffuser serve to provide azimuthally symmetric illumination of the entire finish portion, with a large diversity of ray directions impinging upon the finish. The latter has the effect of ameliorating refractive effects of contour variations in the shape of the finish such as threads. In addition, the large diversity of light ray directions impinging upon the check permits the check to reflect light toward the detector for a large range of check orientations.

The present invention provides a method and apparatus for detecting horizontal checks in the finish portion of transparent containers, wherever they may be located, by illuminating the finish from above. The primary purpose is to enhance the horizontal checks in the prescribed area of the container to allow their ready detection and subsequent rejection of the container by an independent device dedicated to horizontal check detection. This invention illuminates horizontal checks or vertical checks having a horizontal component and makes their detection readily possible.

The present invention lends itself to application to existing inspection machines performing multiple inspecting functions at a series of sequential inspection stations mounted on a circular machine, for example. The apparatus of this invention may be mounted at one of such stations for horizontal check detection.

Various modifications and other embodiments of the present invention may be resorted to within the spirit and scope of the appended claims.

We claim:

1. The method of inspecting glass containers, and the like, for horizontal checks in the finish portion thereof, comprising the steps of
   moving the containers successively in an upright position through an inspection station,
   momentarily interrupting the lateral movement of each container at said inspection station,
   illuminating the entire external finish portion of said container from above with a convergent, annular, diffused pattern of radiant energy to which the said container is transparent,
   and mounting a light-sensitive device having its field of view downwardly through the annular diffused source of radiant energy such that any reflected light from a horizontal check will be imaged onto and caused to energize said light-sensitive device.

2. The method in accordance with claim 1, including the step of creating a signal in response to said energization to effect rejection of a container having a horizontal check in said finish portion.

3. The method in accordance with claim 1, including the step of rejecting a container having a horizontal check in its finish portion in response to the signal from the energization of said light-sensitive device.

4. An apparatus for inspecting glass containers for horizontal checks in the finish portion thereof, wherein the containers are successively moved upright through an inspection station, with means at said inspection station for interrupting lateral movement of said container, the improvement comprising an annular diffused source of radiant energy at said inspection station, said source of radiant energy being positioned above the container finish and coaxial therewith, the spacing therebetween being such as to illuminate the entire external annular surface of the container finish with a downwardly directed, convergent pattern of illumination, a light-sensitive device mounted at said inspection station in axial alignment with the open center of said annular diffused source of radiant energy and above said container to view the interior of the upper area of said finish portion such that a reflected detectable portion of said radiant energy will energize said light-sensitive device, and means for creating a signal in response to the energization of said light-sensitive device by a horizontal check.

5. The combined apparatus set forth in claim 4, wherein said annular diffused source of radiant energy comprises an electric incandescent lamp in the form of an annular ring and a translucent diffuser plate having a central opening disposed intermediate said lamp and said container finish portion.

6. The combined apparatus set forth in claim 4, wherein the said light-sensitive device comprises a video camera, and a wide angle lens positioned axially above the container finish for providing an image of the interior of the container finish, said camera viewing the image produced by said lens.

7. The combined apparatus set forth in claim 4, including means for rejecting a check-bearing finish portion of said container in response to said signal from the energization of said light-sensitive device.

* * * * *